(12) United States Patent
Inhelder et al.

(10) Patent No.: US 7,202,492 B2
(45) Date of Patent: Apr. 10, 2007

(54) APPARATUS AND METHOD FOR DETECTING A FEATURE OF A RUNNING MATERIAL WEB

(75) Inventors: Jörg Inhelder, Bülach (CH); Roland Steininger, Zürich (CH)

(73) Assignee: FMS Force Measuring System AG (CH)

( * ) Notice: Subject to any disclaimer, the term of this patent is extended or adjusted under 35 U.S.C. 154(b) by 0 days.

(21) Appl. No.: 11/196,956

(22) Filed: Aug. 3, 2005

(65) Prior Publication Data

US 2006/0027767 A1    Feb. 9, 2006

(30) Foreign Application Priority Data

Aug. 4, 2003    (EP)    ................................ 04018453

(51) Int. Cl.
*G01N 21/86* (2006.01)
*G01V 8/00* (2006.01)

(52) U.S. Cl. .............................. 250/559.4; 250/559.44; 356/429

(58) Field of Classification Search ........... 250/559.36, 250/559.4, 559.44, 559.29, 205, 214 B; 356/429–431, 356/637, 237.1–237.3, 238.1, 238.2, 239.7, 356/239.8; 362/27

See application file for complete search history.

(56) References Cited

U.S. PATENT DOCUMENTS 5,548,120 A    8/1996   Parker et al. ............ 250/241.7
6,566,670 B1   5/2003   Buisker et al. ......... 250/559.36

FOREIGN PATENT DOCUMENTS

EP    0711995    5/1996
EP    1300353    4/2003

*Primary Examiner*—Stephone B. Allen
*Assistant Examiner*—Suezu Ellis
(74) *Attorney, Agent, or Firm*—K. David Crockett, Esq.; Crockett & Crockett (57) ABSTRACT

An apparatus for detecting a substantially longitudinally extending feature of a running material web, especially the side edge of the web or an applied marker line, comprises a plurality of individually addressable light sources (22-1, to, 22-n) for illuminating, in one of multiple different lighting configurations, a section of the material web (10) containing the feature (12) to be detected; a spatially resolving detection unit (24) for recording the light emitted by the illuminated section as an optical response and for transmitting to an analysis unit (30) a data signal corresponding to the recorded light; an analysis unit (30) for determining, from the transmitted data signal, one or more characteristic parameters of the feature (12) to be detected; and a selection unit (32) for automatically selecting an optimal lighting configuration, which unit is arranged and adapted to address the light sources (22-1, to, 22-n) in different lighting configurations, to rate according to a pre-selected criterion the characteristic parameters determined in each case for the feature (12) to be detected, and on the basis of this rating, to select the optimal lighting configuration for further detection.

36 Claims, 4 Drawing Sheets

APPARATUS AND METHOD FOR DETECTING A FEATURE OF A RUNNING MATERIAL WEB

This application claims priority of European application EP 04018453.3 filed Aug. 4, 2004.

FIELD OF THE INVENTIONS

The invention relates to the field of controlling running material webs and relates especially to an apparatus and a method for detecting a substantially longitudinally extending feature of a running material web, such as the side edge of the material web or a marker line imprinted on the material web.

BACKGROUND OF THE INVENTIONS

In the manufacture and processing of planar material webs, such as paper webs and plastic and metal sheeting, the material webs are guided and transported between rotating rollers. To precisely guide and align the webs, a control loop is used in which the lateral position of the material web constitutes the control variable.

An optical sensor or an ultrasonic sensor continuously detects the position of a longitudinally extending feature, typically the side edge of the material web or an imprinted marker line. From the detected position of the marking, a web travel controller calculates the offset of the web from a specified target position and, if required, drives a pivoted frame forming the actuator such that the material web is laterally guided back to its target position.

Optical line sensors for controlling a material web at a printed line or a material edge are known. In such an optical line sensor, a light transmitter in the sensor generates a light spot on the surface of the material to be scanned. The reflected light is recorded by two triangular photodiodes and analyzed in an analog circuit. Prior to operation, the line sensor must be set to the color contrast of the material to be scanned. To do this, the sensor is manually positioned on a line imprinted on the material web and a certain key sequence is input into the electronics. Then the sensor is directed at the background and a further key sequence is input into the electronics. The sensor is then ready for operation and correctly set. Such sensors are reliable and sturdy, but there are restrictions on the admissible line width of the printed lines, as well as in recognizing different contrasts.

U.S. Pat. No. 6,566,670 B1 describes a system for guiding a web of moving material that includes as illumination sources four multicolored light-emitting diodes that are disposed at different positions relative to the focus point on the material web. To operate the system, an operator selects, according to the reflection properties of the material web (matte, glossy or holographic), the first (for matte webs), the second (for glossy webs) or the third and fourth light-emitting diode together (for webs with holographic properties). Further, the color of the selected light-emitting diode (red, blue, green or infrared) is set depending on the type of material web and the color of the line to be tracked. A disadvantage of this system is that the operator's eye recognizes colors, while the photodiodes of the sensor detect only gray scale values, so that an optimal setting is often difficult to carry out, and is achieved only after several setting procedures by trial and error. Therefore, a new and improved device and method for detecting a feature of a running material web are needed.

SUMMARY

The object of the present invention is to specify a generic apparatus that facilitates simple and reliable detection of a number of different features of running material webs.

According to the present invention, an apparatus is comprised of a plurality of individually addressable light sources for illuminating a section of a material web containing the feature to be detected; a spatially resolving detection unit for recording the light emitted by the illuminated section; an analysis unit for determining from the transmitted data signal one or more characteristic parameters of the feature to be detected; and a selection unit. The selection serves to automatically determine an optical lighting configuration. The selection unit is arranged and adapted to address the light sources in different lighting configurations, to rate according to a pre-selected criterion the characteristic parameters determined in each case for the feature to be detected. Based on this rating, the selection unit determines the optimal lighting configuration for further detection.

The optimal lighting configuration determined by the selection unit can be displayed and, following confirmation by a user, be used for further detection. Preferably, however, the optimal lighting configuration for further detection is employed automatically, that is, with no further user intervention. In a further version, the optimal lighting configuration is normally used automatically and requires user input only in exceptional cases, for instance when the rating lies below a specified minimum value.

The individually addressable light sources can be formed by monochromatic light-emitting diodes, the plurality of light sources can comprise light-emitting diodes of different colors. Red, orange, yellow, green, blue and white, for example, may be used as light-emitting diode colors, as well as colors outside the visible spectral range, such as infrared and ultraviolet.

In another configuration, the individually addressable light sources are disposed in different positions relative to the feature to be detected. In this way, allowance can be made for special reflection properties of the material web or of the feature to be detected, such as a specular or diffusely reflecting character of the material web and/or of the feature to be detected, or a character that reflects only in certain directions, such as for a holographic web or a holographic feature.

As an optical response to the illumination, the illuminated material web section emits light that is recorded by the spatially resolving detection unit. Normally, the emitted light is formed by the light diffusely or specularly reflected by the material web. In the context, however, other emission processes of the material web or the feature are also possible, such as fluorescence emission. For example, a marker line having a fluorescent color can be printed on the material web, and the fluorescence of the marker line can be excited by an ultraviolet component of the illumination spectrum.

The spatially resolving detection unit can be formed by a plurality of photodiodes disposed side by side, or by a plurality of CCD elements disposed side by side, such as a CCD line array. Such a CCD line array is very well suited for detecting a region perpendicular to the extension direction of the feature and for determining its characteristic properties. Economical and fast detection units that exhibit sufficiently high spatial resolution for detecting typical features of running material webs can be realized with relatively short CCD line arrays, for example with 64, 128 or 256 pixel elements.

The analysis unit can include a digital signal processor that facilitates flexible analysis of the feature properties and real-time tracking of the feature for determining the characteristic parameters.

The analysis unit can determine as the characteristic parameter the feature contrast in the cross-web direction and, if applicable, as further parameters, the polarity of the change in lightness of the feature in the cross-web direction and/or the line width of an applied marker line. For a marker edge or a web edge, the difference between the lightness values on both sides of the edge and outside a transition region of a certain width can be used as the feature contrast. For marker lines, the two line edges can be treated separately, and as the total contrast, for example, the minimum value, the maximum value or the mean value of the contrast values of the two edges can be used. The polarity of the change in lightness indicates the transition light→dark or dark→light. The line width is given by the distance between two detected line edges.

After a Fourier transform of the data signal, at least some of the characteristic parameters can also be determined in the frequency domain. Suitable methods, especially for fast Fourier transformation (FFT) and for digital filtering and signal processing in the frequency domain are known to the person of skill in the art.

Finally, the selection unit can determine as the optimal lighting configuration for further detection the lighting configuration that exhibits a maximum feature contrast. This lighting configuration can be automatically used for further detection. If desired, the lighting configuration established as optimal can also be displayed and set only after confirmation by a user.

Another configuration of the apparatus is comprised of an illumination unit for illuminating a section of the material web containing the feature to be detected; a spatially resolving detection unit for recording the light emitted by the illuminated section as an optical response in one of multiple different settable detection configurations, and for transmitting to an analysis unit a data signal corresponding to the recorded light; an analysis unit for determining from the transmitted data signal one or more characteristic parameters of the feature to be detected; and a selection unit for automatically determining an optimal detection configuration that is arranged and adapted to address the detection unit in different of the settable detection configurations, to rate according to a preselected criterion the characteristic parameters determined in each case for the feature to be detected, and based on this rating, to determine the optimal detection configuration for further detection.

The detection unit can include a settable color filter whose different filter settings result in the different settable detection configurations. Alternatively, the detection unit can include multiple detection elements that can be read out selectively and have different spectral sensitivity. In this version, the selection of the detection elements to be read out results in the different settable detection configurations of the detection unit. Here, the selection of the detection configuration can also take place only after the detection elements are read out. For example, detection elements with different spectral sensitivity can be disposed in regular succession and read out together, whereby, depending on the detection configuration, only the data signals of a certain type of detection element are used for analyzing the characteristic parameters.

In calibrating the apparatus, a section of the material web containing the feature to be detected is illuminated. The light emitted as an optical response by the illuminated section is detected, spatially resolved, in one of multiple different settable detection configurations, and a data signal corresponding to the recorded light is generated. One or more characteristic parameters of the feature to be detected are determined from the data signal generated. Here, the detection unit is addressed in different of the settable detection configurations for automatically determining an optimal detection configuration. The characteristic parameters determined in each case for the feature to be detected are rated according to a preselected criterion and the optimal detection configuration for further detection is determined based on this rating.

In another configuration, an apparatus can have both a settable lighting configuration and a settable detection configuration. When detecting a feature of a running material web, a section of the material web containing the feature to be detected is illuminated by one or more individually addressable light sources in a selected lighting configuration. The light emitted by the illuminated section as an optical response is detected, spatially resolved, in one of multiple different settable detection configurations, and a data signal corresponding to the recorded light is generated. One or more characteristic parameters of the feature to be detected are then determined from the data signal generated. For automatically determining an optimal combination of lighting configuration and detection configuration, the light sources are addressed in different lighting configurations. For each lighting configuration, the detection unit is addressed in different of the settable detection configurations. The characteristic parameters determined in each case for the feature to be detected are rated according to a pre-selected criterion, and on the basis of this rating, the optimal combination of lighting configuration and detection configuration for further detection is determined.

BRIEF DESCRIPTION OF THE DRAWINGS

The invention is explained in greater detail below by reference to exemplary embodiments in conjunction with the drawings. Only the elements that are essential to understanding the present invention are depicted.

DETAILED DESCRIPTION OF THE INVENTIONS

Figure 1:
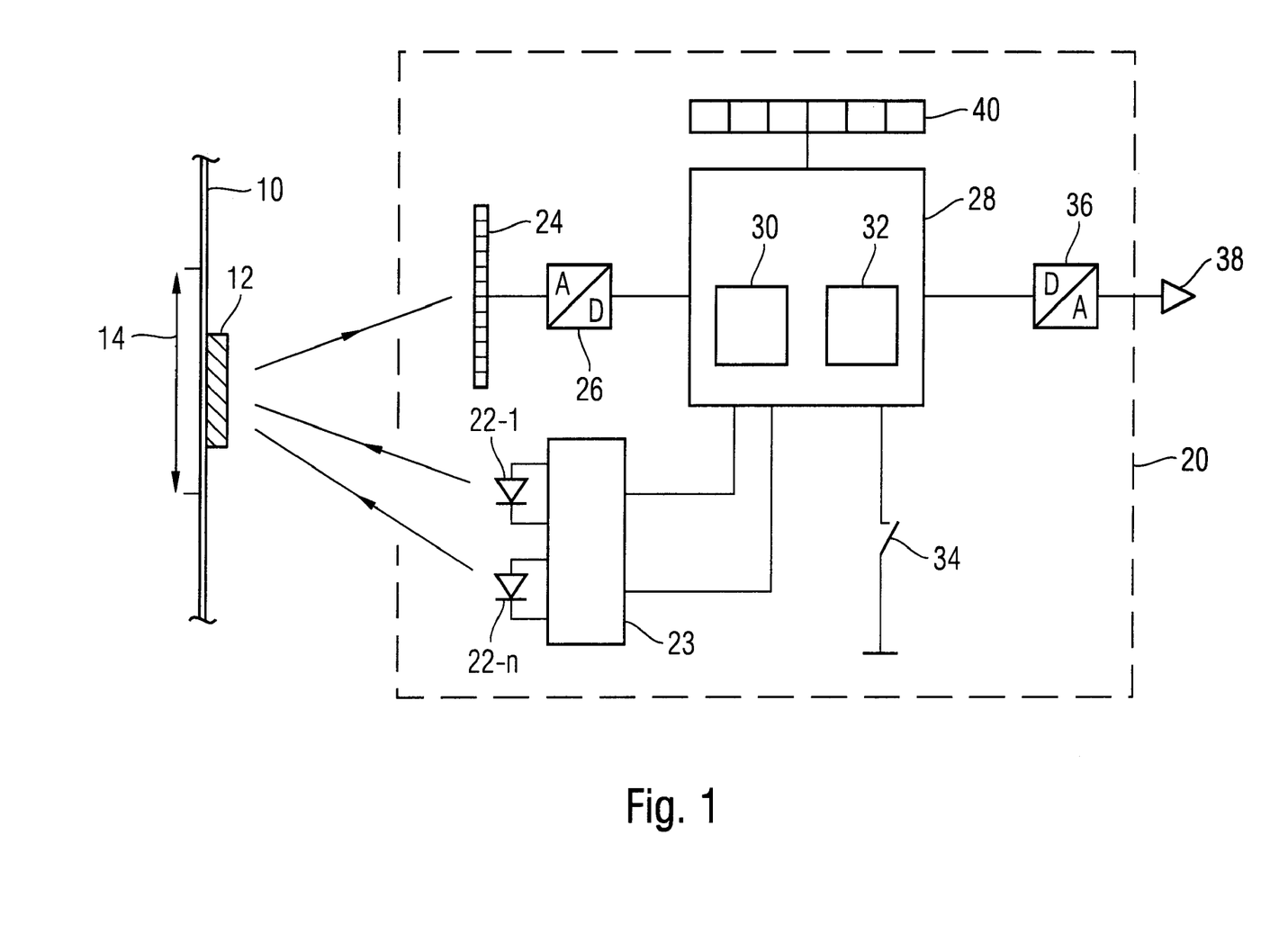
FIG. 1 is a block diagram of a digital line sensor according to an exemplary embodiment of the present invention.

FIG. 1 shows a block diagram of a digital line sensor 20 which detects the position of an imprinted marker line 12 on a material web 10.

For this purpose, the line sensor 20 includes a plurality of individually addressable light-emitting diodes 22-1 to 22-$n$ of different colors that serve to illuminate a section 14 of the material web 10 containing the marker line 12. For the sake of a more comprehensible diagram, FIG. 1 shows only two light-emitting diodes.

However, the use of three or four super bright light-emitting diodes of different colors can also be used. Of course, a larger number of light-emitting diodes also is within the scope of the present invention. As described in greater detail below, for illuminating a material web/marker combination, a certain lighting configuration is used that comprises one or more of the light-emitting diodes 22-1 to 22-n. Here, every combination of the light-emitting diodes 22-1 to 22-n that can be employed for illumination forms a possible lighting configuration.

The light reflected by the illuminated section 14 of the material web 10 is recorded by a CCD line array 24 that contains, in the exemplary embodiment, 128 pixels. In FIG. 1, optical elements not shown, especially lenses and/or mirrors, can be introduced into the light path for both illumination and detection of the detected emission, to improve the illumination of the marking 12 and the CCD line array 24.

The CCD line array 24 is arranged and adapted so that it detects, perpendicular to the direction of longitudinal extension of the marker line 12, a region whose width (transverse extension) is greater than the line width. For example, the CCD line array 24 in the exemplary embodiment detects an 8 mm wide region on the material web 10 and can thus easily detect and track marker lines having line widths between 0.5 mm and about 6 mm.

The output signals of the CCD line array 24 are read out, for example with a clock frequency of 1 MHz, and fed to a fast analog/digital converter 26. The digitized values are read into a digital signal processor (DSP) 28 and buffered. When all pixel values of the CCD line array 24 have been read out and stored in the digital signal processor 28, the analysis unit 30 of the signal processor 28 calculates, program controlled, the predetermined characteristic parameters for the marker line 12.

Figure 2:
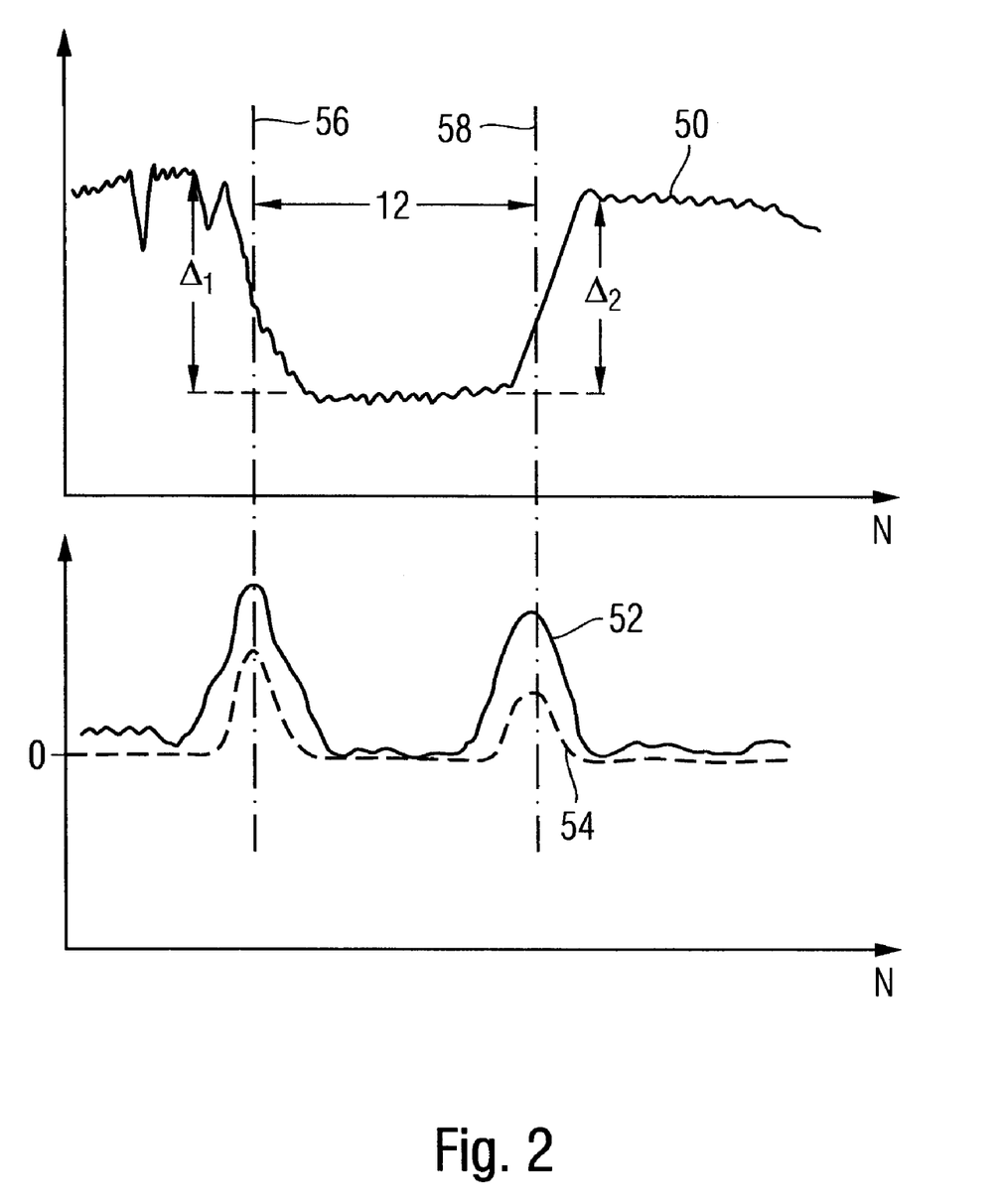
FIG. 2 is two diagrams for explaining the determination of the characteristic parameters of a marker line.

In another configuration, polarity and line width of the marker line 12 are determined as the characteristic parameters. The determination of these parameters will now be explained in greater detail with reference to FIG. 2. For this purpose, FIG. 2 shows, in the upper part of the image, a schematic diagram of a typical raw data curve 50 of the lightness values delivered by the CCD line array 24 in detecting a marker line 12. To smooth out the raw data curve and eliminate individual outlier points, initially, a fifth-order median filter is applied to the raw data values. Then, to filter out high-frequency noise, a first-order low-pass filter is applied in the forward direction and, to compensate for the phase shift generated, a first-order low-pass filter is applied in reverse. Subsequently, the derivative of the data curve is taken and rectified by taking the absolute value to determine the positions with the maximum lightness changes. The data curve obtained in this way is drawn with a solid line in the lower half of the image in FIG. 2 and labeled with reference number 52.

Finally, the data curve 52 is then cut off for signal values below a certain threshold value $S_{thres}$ ($S_{new}=0$, if $S_{old}<S_{thres}$; otherwise, $S_{new}=S_{old}-S_{thres}$), to disregard signal slopes below a certain limit. The resulting curve 54 obtained in this way is drawn as a dotted line in FIG. 2.

The positions 56 and 58 of the maxima of the resulting curve 54 are viewed as the positions of the two edges of the line feature, and the line width and the current position of the line are determined from there. Furthermore, the polarity of the lightness transition (light→dark for edge 56, dark→light for edge 58) is determined for the two edges 56, 58, and the difference of the lightness values outside and within the line ($\Delta_1$ for edge 56, $\Delta_2$ for edge 58) is determined as the feature contrast.

The parameters determined in this way are transferred to a higher-level program component in which the number and the characteristics of the maxima found are compared with the output values. Here, the line marking described in the example yields two maxima with the cited polarities and contrast values. Other line markings, such as a light line on a dark background, can also yield reverse polarity. If an edge marking or the side edge of a web is used as the feature, a single maximum with a polarity light→dark or dark→light is obtained.

If the originally set line or edge is recognized in the higher-level program component, through the digital/analog converter 36 is output an analog signal 38 proportional to the current line or edge position that is used in the web travel control device in the known manner for guiding the material web. In addition to other status messages, the relative position of the tracked line or edge can be output for the user on a display device, such as the LED display 40. If the originally set line or edge is not recognized, an error signal is generated and, for example, displayed on the LED display 40.

The light-emitting diodes 22-1 to 22-n are addressed by a driver 23, individually or in any combination. To reduce the ambient light sensitivity of the sensor 10, in the exemplary embodiment, the light-emitting diodes 22-1 to 22-n are switched on only in the time window in which the CCD line array 24 is ready for recording reflected light. For example, for a total cycle time of 2 ms for illumination, recording and analysis, the light-emitting diodes are switched on only during a 256-µs time window. This makes it possible to operate the light-emitting diodes with a significantly higher current and, as a result, a higher light gain than for continuous-wave operation.

To be able to reliably detect and track a number of different marker lines, the light-emitting diodes 22-1 to 22-n are each formed by super bright, monochrome light-emitting diodes, the totality of the light-emitting diodes 22-1 to 22-n comprising different colors. For example, three super bright light-emitting diodes having the colors red (LED 22-1), white (LED 22-2) and red (LED 22-3), or four super bright light-emitting diodes having the colors red (LED 22-1), blue (LED 22-2), white (LED 22-3) and red (LED 22-4) can be used.

The color and contrast ratio of the given combination of material web and marking is accounted for through an automatic selection of one or more of the light-emitting diodes 22-1 to 22-n of the appropriate color(s), to realize an optimally matched lighting configuration of the light-emitting diodes with no further user intervention. For this purpose, at the beginning of each detection, an automatic setting or calibration of the sensor to the currently given combination of material web and marking is triggered by actuating a corresponding control key 34. The calibration can, of course, also be carried out after a certain operating time or upon a change in the material web/marker combination to obtain new defined input values for the characteristic parameters. Alternatively, a recalibration can also be triggered automatically, for example by an external control signal that indicates a change in the material web/marker combination.

The selection unit 32 addresses the light sources 22-1 to 22-n sequentially in different lighting configurations upon manual or automatic triggering of the calibration. Typically, all possible lighting configurations are used here, but certain configurations can also be excluded through programming, for example because they are not suitable for the type of material web to be guided.

For each lighting configuration that is run through, the characteristic parameters of the feature to be detected, the contrast, polarity and line width, are determined and rated according to a pre-selected criterion, as described above.

The average $(\Delta_1+\Delta_2)/2$ of the contrast values of the two line edges, for example, can be determined as the rating criterion for each of the lighting configurations, and then the configuration selected in which this contrast average is the maximum. According to another criterion, the lighting configuration with the highest individual contrast of one of the two line edges is selected.

However, it has been shown that a particularly stable detection is achieved when the smaller of the contrast values of the two line edges is determined in each case, $A_{min}=\min(\Delta_1, \Delta_2)$, and then the lighting configuration with the maximum $\Delta_{min}$ is selected.

Depending on the marker type, other or additional criteria can be specified without going beyond the scope of the present invention. The pre-selected criterion can also include a complex, multi-stage rating. For example, it can be provided that detection is automatically shifted from line detection to edge detection if none of the above-determined values for $\Delta_{min}$ fulfills certain minimum requirements. For edge detection, the lighting configuration that exhibits the largest contrast value is then selected.

Figure 3:
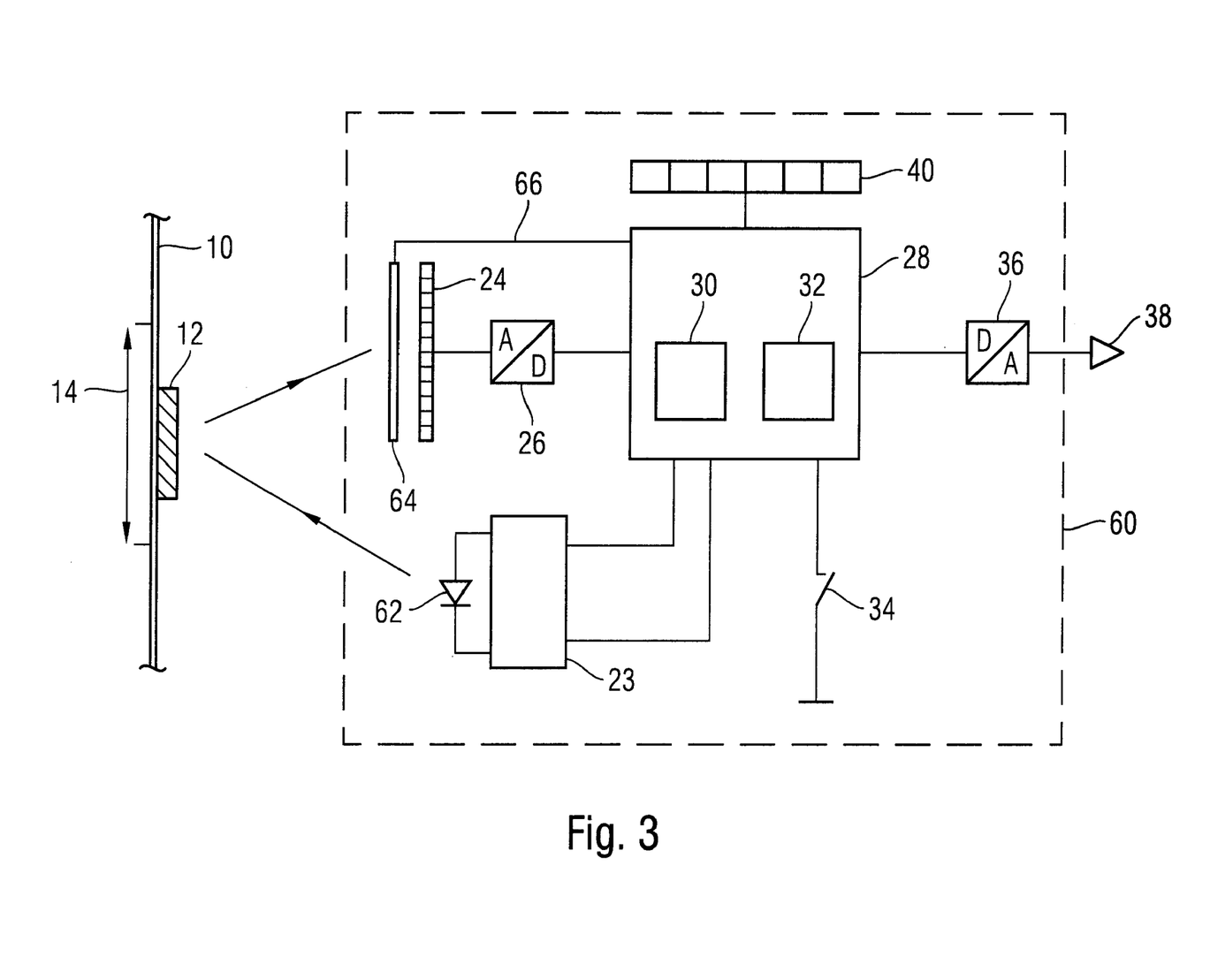
FIG. 3 is a block diagram of a digital line sensor according to another exemplary embodiment of the present invention.

FIG. 3 shows a digital line sensor 60 according to another configuration of the present invention. Here, identical reference numbers to those in FIG. 1 indicate identical elements. In contrast to FIG. 1, the line sensor 60 does not include a plurality of light-emitting diodes, but rather only a single wide-band, for example white light-emitting diode 62 for illuminating the material web section 14.

The light reflected by the section 14 reaches the CCD line array 24 via a settable color filter 64. The settable color filter 64 can be formed, for example, by a rotating filter disc with individual filter elements of different colors, that is driven by the DSP 28 (reference number 66). Alternatively, the color filter 64 is formed by a voltage-controlled filter element whose spectral transmission behavior can be varied by an applied bias voltage.

Rather than the optimal lighting configuration, as in FIG. 1, the optimal detection configuration is determined by setting of the color filter 64 with which the highest rating is achieved for the respective characteristic parameters.

For this purpose, when calibrating the line sensor 60 to the current combination of material web and marking, the selection unit 32 sets different filter settings for the color filter 64. The light reflected by the illuminated section 14, filtered accordingly, reaches the CCD line array 24, where it is recorded and converted to an electrical data signal. As described for FIG. 1, the characteristic parameters are determined from the data signal and rated according to a pre-selected criterion. The filter setting with the highest rating, for example with the highest feature contrast, is selected as the detection configuration for further detection.

Figure 4:
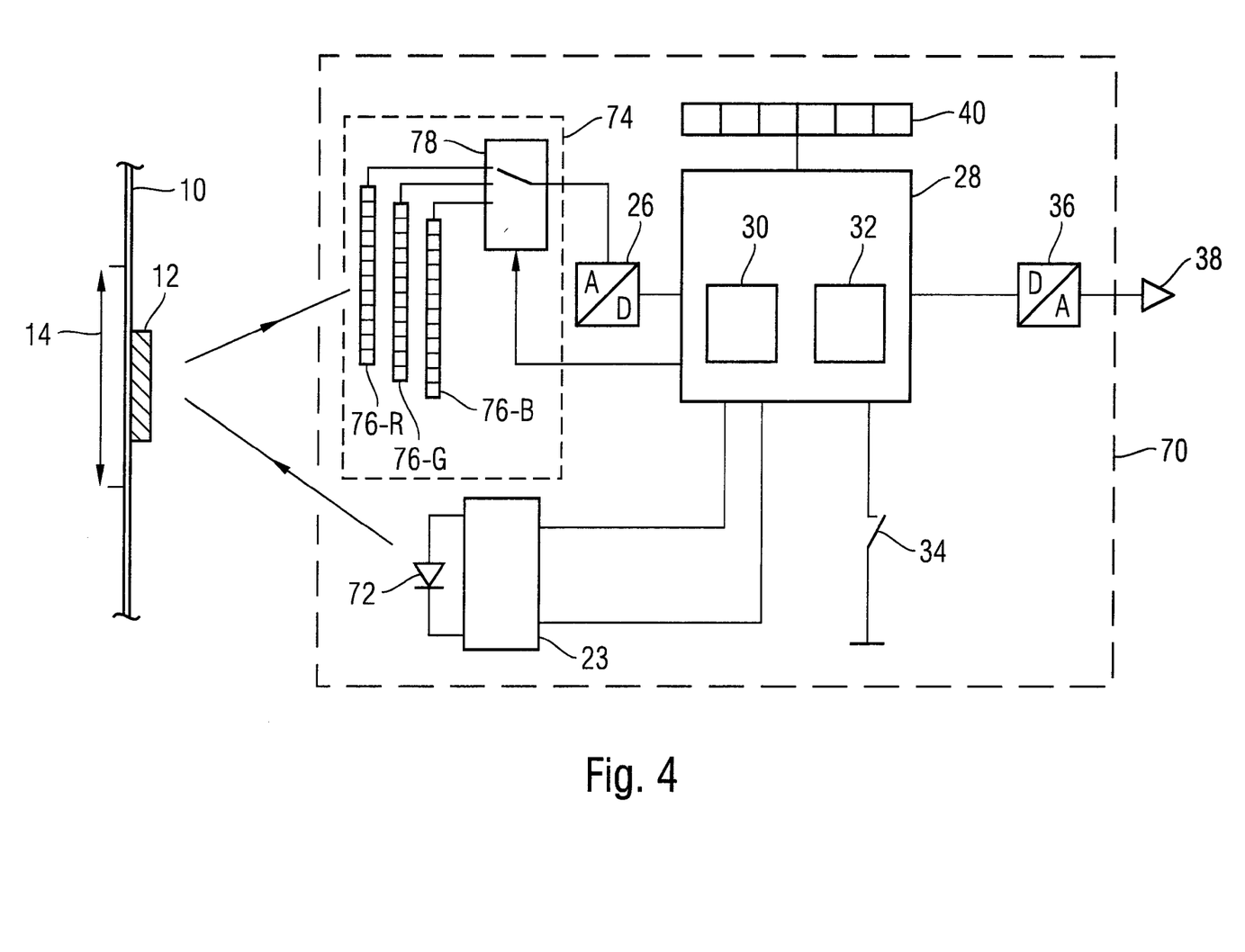
FIG. 4 is a block diagram of a digital line sensor according to a further exemplary embodiment of the present invention.

A further configuration is shown in FIG. 4. The digital line sensor 70 exhibits, like the line sensor 60 in FIG. 3, merely a single wide-band light-emitting diode 72 for illuminating the material web section 14. The light reflected by the material web is recorded by a detection unit 74 that includes three CCD line arrays 76-R, 76-G and 76-B with maximum sensitivities in the red (76-R), green (76-G) and blue (76-B) spectral range. A multiplexer 78 addressed by the DSP 28 defines which of the CCD line arrays is read out. For example, in the situation in FIG. 4, the red-sensitive CCD line array 76-R is read out and only its data signals are directed to the analog/digital converter 26. This can be advantageous, for example, for a blue or green marker line on a white ground, since the marker line appears with the highest contrast to the red-sensitive CCD line array.

To automatically select the most favorable CCD line array, the sensor 70 is calibrated at the start of detection. To do this, the selection unit 32 addresses the light-emitting diode 72 and the multiplexer 78 such that the CCD line arrays 76-R, 76-G and 76-B are read out in succession with constant illumination. The CCD line array whose data signals yield the highest rating for the characteristic parameters is selected for further detection.

Compared with a selection to be specified by the user, the described automatic determination of the optimal lighting configuration or the optimal detection configuration results in substantially more reliable and robust feature detection. Since the complex interactions between the type and color of the material web, the type and color of the applied marking, the color or the spectral distribution of the illumination sources, the illumination geometry and the illumination of the feature region are difficult for the human eye to judge, but can be correctly accounted for by the method according to the present invention.

While the invention has been shown and described with particular reference to preferred exemplary embodiments, it will be understood by the person skilled in the art that changes in the form and detail can be made without departing from the spirit and scope of the present invention. For example, the light sources, detection unit, analysis unit and selection unit in each of the exemplary embodiments are combined in a shared sensor housing. It is understood, however, that these units can also be designed as separate, co-acting units.

Also, a unit can assume more than one function. For example, in the exemplary embodiments, the digital signal processor includes both the analysis unit and the selection unit. In another configuration, in addition to recording the light, an "intelligent" CCD line array could also determine the characteristic parameters, and thus function both as a detection unit and as an analysis unit.

Accordingly, the disclosure of the present invention is not intended to be limiting. Instead, the disclosure of the present invention is intended to exemplify the scope of the present invention as set forth in the appended claims.

We claim:

1. An apparatus for detecting a substantially longitudinally extending feature of a running material web comprising:
   a plurality of individually addressable light sources for illuminating, in one of multiple different lighting configurations, a section of the material web containing the feature to be detected;
   a spatially resolving detection unit for recording the light emitted by the illuminated section as an optical response and for transmitting to an analysis unit a data signal corresponding to the recorded light;
   an analysis unit for determining from the transmitted data signal one or more characteristic parameters of the feature to be detected; and
   a selection unit for automatically determining an optimal lighting configuration, that is arranged and adapted to address the light sources in different lighting configurations, to rate according to a preselected criterion the characteristic parameters determined in each case for the feature to be detected, and based on this rating, to determine the optimal lighting configuration for further detection.

2. The apparatus according to claim 1, wherein the individually addressable light sources are formed by monochrome light-emitting diodes of different colors.

3. The apparatus according to claim 1, wherein, the individually addressable light sources are disposed in various positions relative to the feature to be detected.

4. The apparatus according to claim 1, wherein the spatially resolving detection unit is formed by a plurality of photodiodes disposed side by side.

5. The apparatus according to claim 1, wherein the spatially resolving detection unit is formed by a plurality of CCD elements disposed side by side.

6. The apparatus according to claim 1, wherein the analysis unit for determining the characteristic parameters includes a digital signal processor.

7. The apparatus according to claim 1, wherein the analysis unit determines the feature contrast in the cross-web direction and the polarity of the change in lightness of the feature in the cross-web direction and the line width of an applied marker line.

8. The apparatus according to claim 7, wherein the selection unit determines the lighting configuration with maximum feature contrast as the optimal lighting configuration for further detection.

9. A method for detecting a substantially longitudinally extending feature of a running material web in which:
- a section of the material web containing the feature to be detected is illuminated by one or more individually addressable light sources in a selected lighting configuration;
- the light emitted by the illuminated section as an optical response is detected, spatially resolved, and a data signal corresponding to the detected light is generated;
- one or more characteristic parameters of the feature to be detected are determined from the data signal generated; and
- the light sources are addressed in different lighting configurations, the characteristic parameters determined in each case for the feature to be detected are rated according to a pre-selected criterion, and based on this rating, an optimal lighting configuration for further detection is determined.

10. The method according to claim 9, wherein the lighting configuration determined to be optimal is automatically set for further detection.

11. The method according to claim 9, wherein the automatic determination of the optimal lighting configuration is carried out at least once on user demand.

12. The method according to claim 9, wherein the contrast of the feature to be detected in the cross-web direction is determined as the characteristic parameter, and as additional parameters, the polarity of the change in lightness of the feature of the feature to be detected in the cross-web direction or the line width of an applied marker line are detected.

13. The method according to claim 12, wherein in the automatic determination, the lighting configuration with maximum feature contrast is determined as the optimal lighting configuration for further detection.

14. An apparatus for detecting a substantially longitudinally extending feature of a running material web comprising:
- an illumination unit for illuminating a section of the material web containing the feature to be detected;
- a spatially resolving detection unit for recording the light emitted by the illuminated section as an optical response in one of multiple different settable detection configurations, and for transmitting to an analysis unit a data signal corresponding to the recorded light;
- an analysis unit for determining from the transmitted data signal one or more characteristic parameters of the feature to be detected; and
- a selection unit for automatically determining an optimal detection configuration that is arranged and adapted to address the detection unit in the different settable detection configurations, to rate according to a pre-selected criterion the characteristic parameters determined in each case for the feature to be detected, and based on this rating, to determine the optimal detection configuration for further detection.

15. The apparatus according to claim 14, wherein, the detection unit includes a settable color filter whose different filter settings result in the different settable detection configurations.

16. The apparatus according to claim 14, wherein the detection unit includes multiple detection elements that can be read out selectively and have different spectral sensitivity, in which unit the selection of the detection elements to be read out results in the different settable detection configurations.

17. A method for detecting a substantially longitudinally extending feature of a running material web in which:
- a section of the material web containing the feature to be detected is illuminated;
- the light emitted by the illuminated section as an optical response is detected, spatially resolved, in one of multiple different settable detection configurations, and a data signal corresponding to the detected light is generated;
- one or more characteristic parameters of the feature to be detected are determined from the data signal generated; and
- the detection unit for automatically determining an optimal detection configuration is addressed in different of the settable detection configurations, the characteristic parameters determined in each case for the feature to be detected are rated according to a pre-selected criterion, and based on this rating, the optimal detection configuration for further detection is determined.

18. A method f or detecting a substantially longitudinally extending feature of a running material web in which:
- a section of the material web containing the feature to be detected is illuminated by one or more individually addressable light sources in a selected lighting configuration;
- the light emitted by the illuminated section as an optical response is detected, spatially resolved, in one of multiple different settable detection configurations, and a data signal corresponding to the detected light is generated;
- one or more characteristic parameters of the feature to be detected are determined from the data signal generated; and
- the light sources are addressed in different lighting configurations, for each lighting configuration, the detection unit in different settable detection configurations is addressed, the characteristic parameters determined in each case for the feature to be detected are rated according to a pre-selected criterion, and based on this rating, an optimal combination of lighting configuration and detection configuration for further detection is determined.

19. An apparatus for detecting a substantially longitudinally extending feature of a running material web comprising:

a plurality of individually addressable light sources for illuminating, in one of multiple different lighting configurations, a section of the material web containing the feature to be detected;

a spatially resolving detection unit for recording the light reflected by the illuminated section as an optical response and for transmitting to an analysis unit a data signal corresponding to the recorded light;

an analysis unit for determining from the transmitted data signal one or more characteristic parameters of the feature to be detected; and a selection unit for automatically determining an optimal lighting configuration, that is arranged and adapted to address the light sources in different lighting configurations, to rate according to a preselected criterion the characteristic parameters determined in each case for the feature to be detected, and based on this rating, to determine the optimal lighting configuration for further detection.

20. The apparatus according to claim 19, wherein the individually addressable light sources are formed by monochrome light-emitting diodes of different colors.

21. The apparatus according to claim 19, wherein, the individually addressable light sources are disposed in various positions relative to the feature to be detected.

22. The apparatus according to claim 19, wherein the spatially resolving detection unit is formed by a plurality of photodiodes disposed side by side.

23. The apparatus according to claim 19, wherein the spatially resolving detection unit is formed by a plurality of CCD elements disposed side by side.

24. The apparatus according to claim 19, wherein the analysis unit for determining the characteristic parameters includes a digital signal processor.

25. The apparatus according to claim 19, wherein the analysis unit determines the feature contrast in the cross-web direction and the polarity of the change in lightness of the feature in the cross-web direction and the line width of an applied marker line.

26. The apparatus according to claim 25, wherein the selection unit determines the lighting configuration with maximum feature contrast as the optimal lighting configuration for further detection.

27. A method for detecting a substantially longitudinally extending feature of a running material web in which:

a section of the material web containing the feature to be detected is illuminated by one or more individually addressable light sources in a selected lighting configuration;

the light reflected by the illuminated section as an optical response is detected, spatially resolved, and a data signal corresponding to the detected light is generated;

one or more characteristic parameters of the feature to be detected are determined from the data signal generated; and the light sources are addressed in different lighting configurations, the characteristic parameters determined in each case for the feature to be detected are rated according to a pre-selected criterion, and based on this rating, an optimal lighting configuration for further detection is determined.

28. The method according to claim 27, wherein the lighting configuration determined to be optimal is automatically set for further detection.

29. The method according to claim 27, wherein the automatic determination of the optimal lighting configuration is carried out at least once on user demand.

30. The method according to claim 27, wherein the contrast of the feature to be detected in the cross-web direction is determined as the characteristic parameter, and as additional parameters, the polarity of the change in lightness of the feature of the feature to be detected in the cross-web direction or the line width of an applied marker line are detected.

31. The method according to claim 30, wherein in the automatic determination, the lighting configuration with maximum feature contrast is determined as the optimal lighting configuration for further detection.

32. An apparatus for detecting a substantially longitudinally extending feature of a running material web comprising:

an illumination unit for illuminating a section of the material web containing the feature to be detected;

a spatially resolving detection unit for recording the light reflected by the illuminated section as an optical response in one of multiple different settable detection configurations, and for transmitting to an analysis unit a data signal corresponding to the recorded light;

an analysis unit for determining from the transmitted data signal one or more characteristic parameters of the feature to be detected; and a selection unit for automatically determining an optimal detection configuration that is arranged and adapted to address the detection unit in the different settable detection configurations, to rate according to a preselected criterion the characteristic parameters determined in each case for the feature to be detected, and based on this rating, to determine the optimal detection configuration for further detection.

33. The apparatus according to claim 32, wherein, the detection unit includes a settable color filter whose different filter settings result in the different settable detection configurations.

34. The apparatus according to claim 32, wherein the detection unit includes multiple detection elements that can be read out selectively and have different spectral sensitivity, in which unit the selection of the detection elements to be read out results in the different settable detection configurations.

35. A method for detecting a substantially longitudinally extending feature of a running material web in which:

a section of the material web containing the feature to be detected is illuminated;

the light reflected by the illuminated section as an optical response is detected, spatially resolved, in one of multiple different settable detection configurations, and a data signal corresponding to the detected light is generated;

one or more characteristic parameters of the feature to be detected are determined from the data signal generated; and the detection unit for automatically determining an optimal detection configuration is addressed in different of the settable detection configurations, the characteristic parameters determined in each case for the feature to be detected are rated according to a pre-selected criterion, and based on this rating, the optimal detection configuration for further detection is determined.

36. A method for detecting a substantially longitudinally extending feature of a running material web in which: a section of the material web containing the feature to be detected is illuminated by one or more individually addressable light sources in a selected lighting configuration;

the light reflected by the illuminated section as an optical response is detected, spatially resolved, in one of multiple different settable detection configurations, and a data signal corresponding to the detected light is generated;

one or more characteristic parameters of the feature to be detected are determined from the data signal generated; and the light sources are addressed in different lighting configurations, for each lighting configuration, the detection unit in different settable detection configurations is addressed, the characteristic parameters determined in each case for the feature to be detected are rated according to a pre-selected criterion, and based on this rating, an optimal combination of lighting configuration and detection configuration for further detection is determined.

* * * * *